(12) United States Patent
Smith et al.

(10) Patent No.: US 9,968,416 B2
(45) Date of Patent: May 15, 2018

(54) OPHTHALMIC ILLUMINATION SYSTEMS, DEVICES, AND METHODS

(71) Applicant: Novartis AG, Basel (CH)

(72) Inventors: Ronald T. Smith, Irvine, CA (US); Alireza Mirsepassi, Irvine, CA (US)

(73) Assignee: NOVARTIS AG (CH)

(*) Notice: Subject to any disclaimer, the term of this patent is extended or adjusted under 35 U.S.C. 154(b) by 74 days.

(21) Appl. No.: 15/051,422

(22) Filed: Feb. 23, 2016

(65) Prior Publication Data

US 2017/0172693 A1 Jun. 22, 2017

Related U.S. Application Data

(60) Provisional application No. 62/268,359, filed on Dec. 16, 2015.

(51) Int. Cl.
| | |
|---|---|
| *A61B 90/30* | (2016.01) |
| *A61B 3/00* | (2006.01) |
| *A61B 3/10* | (2006.01) |
| *G02B 19/00* | (2006.01) |
| *G02B 27/14* | (2006.01) |
| *G02B 6/24* | (2006.01) |
| *A61F 9/007* | (2006.01) |

(52) U.S. Cl.
CPC ............ *A61B 90/30* (2016.02); *A61B 3/0008* (2013.01); *A61B 3/10* (2013.01); *G02B 6/24* (2013.01); *G02B 19/0028* (2013.01); *G02B 19/0047* (2013.01); *G02B 27/141* (2013.01); *A61B 2090/306* (2016.02); *A61F 9/007* (2013.01)

(58) Field of Classification Search
CPC ......... A61B 3/0008; A61B 3/10; A61B 90/30; A61B 2090/306; G02B 6/24; G02B 19/0028; G02B 19/0047; G02B 27/141; A61F 9/007
See application file for complete search history.

(56) References Cited

U.S. PATENT DOCUMENTS

| | | | |
|---|---|---|---|
| 2006/0007538 A1* | 1/2006 | Robinson | G02B 27/102 |
| | | | 359/487.04 |
| 2007/0189664 A1 | 8/2007 | Anderson | |
| 2008/0291397 A1* | 11/2008 | Tesar | A61B 3/12 |
| | | | 351/221 |
| 2010/0309549 A1 | 12/2010 | Luecke et al. | |
| 2012/0203075 A1 | 8/2012 | Horvath et al. | |
| 2014/0058367 A1 | 2/2014 | Dantus | |

(Continued)

*Primary Examiner* — Jordan Schwartz

(57) ABSTRACT

Systems, apparatuses, and methods of and for an ophthalmic illumination system are disclosed. In an exemplary implementation, an ophthalmic illumination system includes a collimator having at least one lens. The system includes a first mirror arranged to reflect light towards the collimator. The first mirror is configured for use with a first light source that emits a first light beam having a first parameter. The system includes a second mirror arranged to reflect light towards the collimator. The second mirror is configured for use with a second light source emitting a second light beam having a second parameter that is different than the first parameter. The second mirror is shaped and arranged to cause a reflected portion of the second light beam to have the first parameter. The first mirror and the first light source, and the second mirror and the second light source, are separately usable with the collimator.

20 Claims, 7 Drawing Sheets

(56) References Cited

U.S. PATENT DOCUMENTS

2015/0294468 A1* 10/2015 Shimizu ............. G01B 9/02091
356/479
2016/0128557 A1   5/2016 Papac et al.
2016/0346058 A1* 12/2016 Bacher .................. A61B 90/30

* cited by examiner

OPHTHALMIC ILLUMINATION SYSTEMS, DEVICES, AND METHODS

CROSS REFERENCE TO RELATED APPLICATIONS

This application claims the benefit of U.S. Provisional Application No. 62/268,359, filed Dec. 16, 2015, the contents of which are incorporated herein by reference.

TECHNICAL FIELD

The present disclosure is directed to ophthalmic illumination devices, systems, and methods. More particularly, but not by way of limitation, the present disclosure is directed to devices, systems, and methods of maintaining the same numerical aperture for a light beam transmitted towards a surgical field using different light source/mirror combinations.

BACKGROUND

Ophthalmic microsurgical procedures frequently require precision cutting and/or removing of various body tissues of the eye. During the procedures, ophthalmic illumination probes may provide illumination for the surgical field. A user, such as a surgeon or other medical professional, may insert the probe into the eye to illuminate the inside of the eye. The probe delivers light using an optical fiber. Typically, the probe is connected to an optical port of an ophthalmic illumination system. The ophthalmic illumination system may be part of a surgical console and includes a light source. The illumination system may also include other optical elements, such as a condenser, that facilitate coupling the light into the probe's optical fiber.

During assembly of the ophthalmic illumination system, manufacturers try to optimize various parameters of the light beam. These parameters may include coupling efficiency, which describes how well the light is coupled into probe's optical fiber. High coupling efficiency corresponds to the desirable transmission of relatively greater amount of undistorted light from the light source to the surgical field, via the probe. Low coupling efficiency corresponds to less light being transmitted to the surgical field, as well as the light that is transmitted having an undesired angular profile. Other parameters that affect system performance include how well the light is transmitted within the fiber and the angular profile of the output beam that is transmitted to the surgical field.

One or more of these parameters may be influenced by the numerical aperture ("NA") of the light beam. The NA is, generally speaking, a description of the width or diameter of a beam and may be referenced as a cone angle. The NA may also be used to describe the width or diameter of a beam that can be accepted by an optical fiber. For some light sources, such as a supercontinuum laser source, the NA of the beam is roughly proportional to wavelength. Thus, higher wavelength light has a higher NA and vice versa. Different light sources can also transmit light having different NAs. Differing beam diameters for different light sources and different wavelengths of light present challenges in manufacturing a system with consistent NA to consistently achieve high levels of coupling efficiency, high transmittance efficiency within the fiber, and desirable angular profiles for the output beam.

Various components of illumination systems, such as collimators, are typically designed to work best with light having a given beam diameter. For example, when a light beam has a collimated beam diameter that is larger than the intended beam diameter, the cone angle of light focused into the fiber will be larger as well. In general, the nominal collimated beam diameter may be maximized to completely angularly fill the acceptance NA of the fiber. Therefore, a collimated beam diameter that is larger than nominal will result in loss of efficiency within the fiber. Even if the beam is efficiently coupled into the fiber, at its first encounter with the core/cladding interface on the cylindrical side surface of the fiber, the high angle rays of the high NA beam above the fiber acceptance NA will be lost in the cladding. Similarly, if the collimated beam diameter is less than the nominal value, the beam will efficiently couple into and be efficiently transmitted through the fiber. However, its beam NA will be less than nominal, and therefore the beam emitted from the distal end of the fiber will have an angular spread that is less than desired. In both circumstances, there is a penalty for not having the collimated beam diameter be constant with wavelength at the nominal desired value. Achieving a consistent collimated beam diameter with different light sources across different wavelengths can be difficult.

SUMMARY

According to one aspect, the present disclosure describes an ophthalmic illumination system including a collimator including a plurality of lenses. The system may include a first mirror arranged to reflect light towards the collimator. The first mirror may be configured for use with a first light source. The first light source may emit a first light beam having a first parameter. The system may also include a second mirror arranged to reflect light towards the collimator. The second mirror may be configured for use with a second light source. The second light source may emit a second light beam having a second parameter that is different than the first parameter. The second mirror may be shaped and arranged to cause a reflected portion of the second light beam to have the first parameter. The first mirror and the first light source, and the second mirror and the second light source, may be separately usable with the collimator.

Another aspect of the present disclosure is directed to an ophthalmic illumination system including a supercontinuum laser source emitting a light beam. The system may also include a mirror reflecting a portion of the light beam. The mirror may be a hyperbolic dichroic mirror or elliptical dichroic mirror. The system may also include an achromatic collimator having a plurality of lenses. The plurality of lenses may transmit the reflected portion of the light beam towards an eye of a patient.

A third aspect of the disclosure is directed to method of manufacturing an ophthalmic illumination system. The method may include selecting a supercontinuum laser source from among multiple supercontinuum laser sources. Each of the multiple supercontinuum laser sources may be arranged to emit a light beam having a respective numerical aperture. The method may also include selecting a dichroic mirror from among multiple dichroic mirrors, based on the selected supercontinuum laser source. At least one parameter associated with a shape of each of the dichroic mirrors may be different. The method may also include obtaining an achromatic collimator having multiple lenses. The selected mirror may be configured to reflect a portion of the light beam towards the achromatic collimator. The method may also include arranging the selected supercontinuum laser source and the selected mirror such that the reflected portion of the light beam has the same numerical aperture for each combination of selected supercontinuum laser source and selected mirror.

The various aspects of the disclosure may include one or more of the following features. The collimator may comprise an achromatic collimator. At least one of the first mirror and the second mirror may comprise a hyperbolic dichroic mirror. The collimator and at least one of the first mirror and second mirror may be disposed within a surgical console. The first mirror may be disposed within a first housing, the second mirror may be disposed within a second housing, and at least one of the plurality of lenses of the collimator may be disposed within a third housing. The first housing and second housing may be sized and shaped to be interchangeably coupled to the third housing. The first and second parameters may be first and second numerical apertures, respectively. The first mirror may be spaced from the first light source by a first distance, and the second mirror may be spaced from the second light source by a second distance. The system may further include the first and second light sources. The first and second light sources may be separately usable with the collimator. At least one of the first and second light sources may be a supercontinuum laser source. At least one of the first mirror and the second mirror may comprise an elliptical dichroic mirror. The system may further include a surgical console. The supercontinuum laser source, the mirror, and the achromatic collimator may be disposed within the surgical console. The system may further include an endo-illuminator in communication with the surgical console. The endo-illuminator may deliver the reflected portion of the light beam into the eye of the patient.

The various aspects of the disclosure may also include one or more of the following features. Arranging the selected supercontinuum laser source and the selected mirror may include spacing the selected supercontinuum laser source and the selected mirror at a first distance. Another of the multiple supercontinuum laser sources and another of the multiple mirrors may be spaced at a second distance for the reflected portion of the light beam to have the same numerical aperture. Arranging the selected supercontinuum laser source and the selected mirror may include coupling the achromatic collimator and a housing comprising the selected supercontinuum laser source and the selected mirror. The selected mirror may be disposed within a first housing, another of the multiple mirrors may be disposed within a second housing, and the multiple lenses of the achromatic collimator may be disposed within a third housing. The first and second housings may be configured to be separately coupled to the third housing. The selected mirror may comprise a hyperbolic mirror. The selected mirror may comprise an elliptical mirror.

It is to be understood that both the foregoing general description and the following drawings and detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following.

BRIEF DESCRIPTION OF THE DRAWINGS

The accompanying drawings illustrate embodiments of the systems, devices, and methods disclosed herein and together with the description, serve to explain the principles of the present disclosure.

Figure 1:
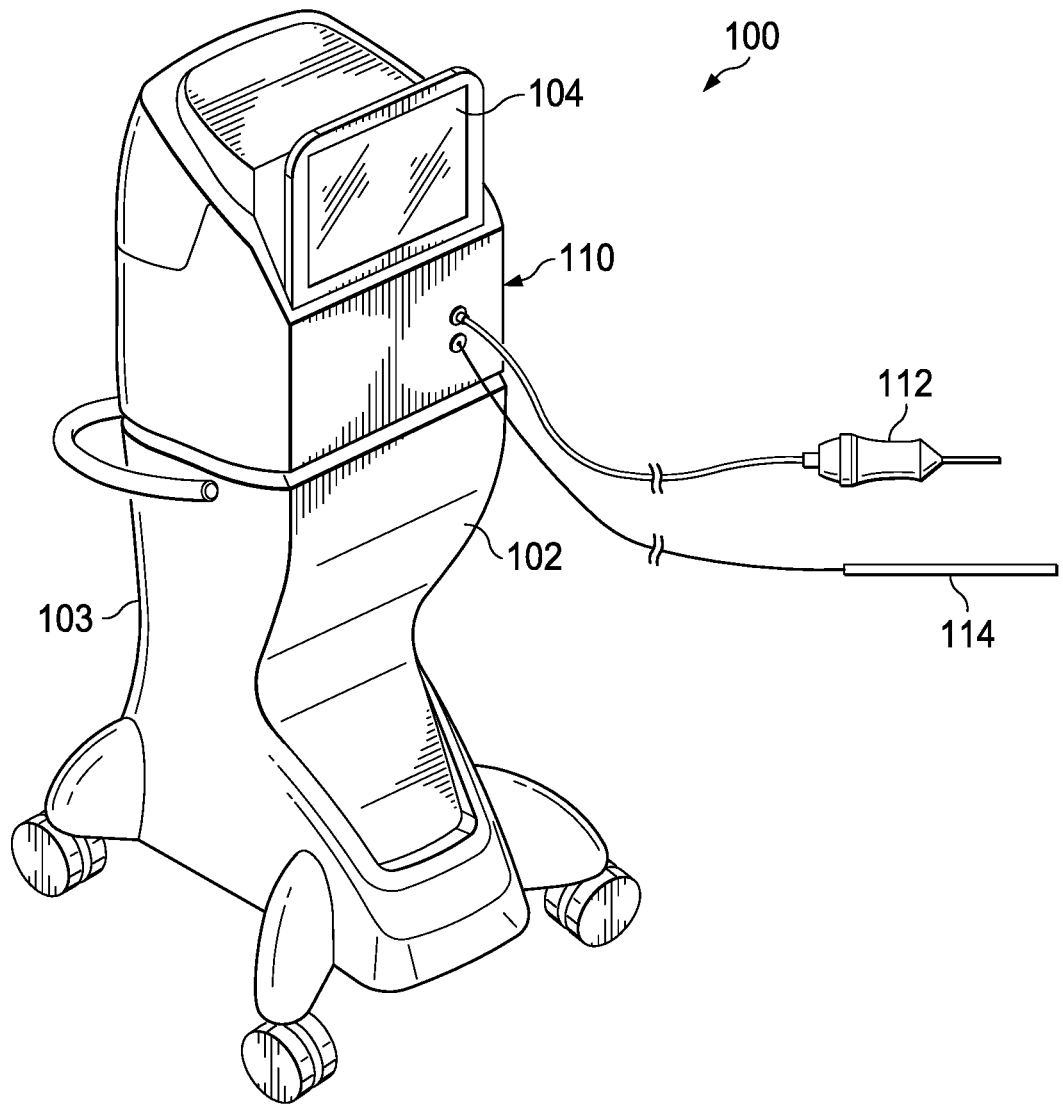
FIG. 1 is an illustration of an example ophthalmic surgical system.

These figures will be better understood by reference to the following detailed description.

DETAILED DESCRIPTION

For the purposes of promoting an understanding of the principles of the present disclosure, reference will now be made to the implementations illustrated in the drawings and specific language will be used to describe them. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with reference to one or more implementations may be combined with the features, components, and/or steps described with reference to other implementations of the present disclosure. For simplicity, in some instances the same reference numbers are used throughout the drawings to refer to the same or like parts.

The present disclosure relates generally to devices, systems, and methods for ensuring that a laser beam entering a collimator in an ophthalmic illumination system has the same or substantially the same numerical aperture ("NA") regardless of the supercontinuum source from which the beam originates. A dichroic mirror that is hyperbolically or elliptically shaped is positioned relative to the light source such that the reflected portion of the light beam has the same NA even though the NAs of the beams emitted by the multiple supercontinuum sources are different. The shape of the mirror and the distance between the mirror and the light source may be selected to achieve the same NA for all mirror/light source combinations.

The devices, systems, and methods of the present disclosure provide numerous advantages. In particular, assembly line manufacturing of the ophthalmic illumination system is simplified because many components of the system, such as the collimator, may stay the same irrespective of different supercontinuum sources. Because the same collimator is used, the advantages of the collimator may be enjoyed for multiple supercontinuum sources. These advantages include good achromatic collimation with a near-diffraction limited collimated wavefront and a collimated beam diameter that is virtually constant with wavelength. These advantages allow for a high coupling efficiency to be obtained even though different supercontinuum sources may be used. Additionally, the systems described herein mitigate the undesired loss of transmittance within the optical fiber due to high angle rays being lost in the cladding as well as provide a desired angular profile for the output beam. The advantages also provide one, such as a manufacturer, a greater flexibility in choosing among supercontinuum sources, based on, for example, cost, availability, and other factors, without sacrificing on performance.

FIG. 1 illustrates an example ophthalmic surgical system 100. The system 100 includes a surgical console 102, a probe 112, and an illuminator 114. The probe 112 and the illuminator 114 may be at least partially positioned within the surgical field or surgical site while a user performs surgical tasks on an eye of a patient. The system 100 may be used to perform various ophthalmic surgical procedures including an anterior segment procedure, a posterior segment procedure, a vitreoretinal procedure, a vitrectomy procedure, a cataract procedure, and/or other desired procedures. The surgical console 102 includes a mobile base housing 103 and an associated display screen 104 showing data relating to system operation and performance during a procedure. A distal portion of probe 112 may be inserted into the eye to treat an optical condition. For example, the probe 112 can be a cutting probe, a vitrectomy probe, a phacoemulsification probe, a laser probe, an ablation probe, a vacuum probe, a flushing probe, scissors, forceps, an infusion device, an aspiration device, and/or other suitable surgical device. The illuminator 114 may have a distal portion configured to be inserted into the eye and illuminate the tissue inside the eye during the surgical procedure. For example, the illuminator 114 may be an ophthalmic chandelier, spot illuminator, endo-illuminator, fiber optic light source, and/or other suitable surgical illumination device. The illuminator 114 may provide bright, background, broadband, and/or white light to illuminate the surgical field. While the probe 112 and the illuminator 114 are shown as distinct components, it is understood that the two may be integrated into a single surgical instrument in some implementations.

The surgical console 102 includes a control system 110 that is communicatively coupled to the probe 112 and/or the illuminator 114. For example, pneumatic, optical, and/or electrical supply lines may extend between and communicatively couple the control system 110 and the probe 112, and/or the illuminator 114. In some implementations, the supply lines may facilitate control and monitoring by also transmitting control signals, status signals, and/or other data between the surgical console 102 and the probe 112 and/or the illuminator 114.

Figure 2:
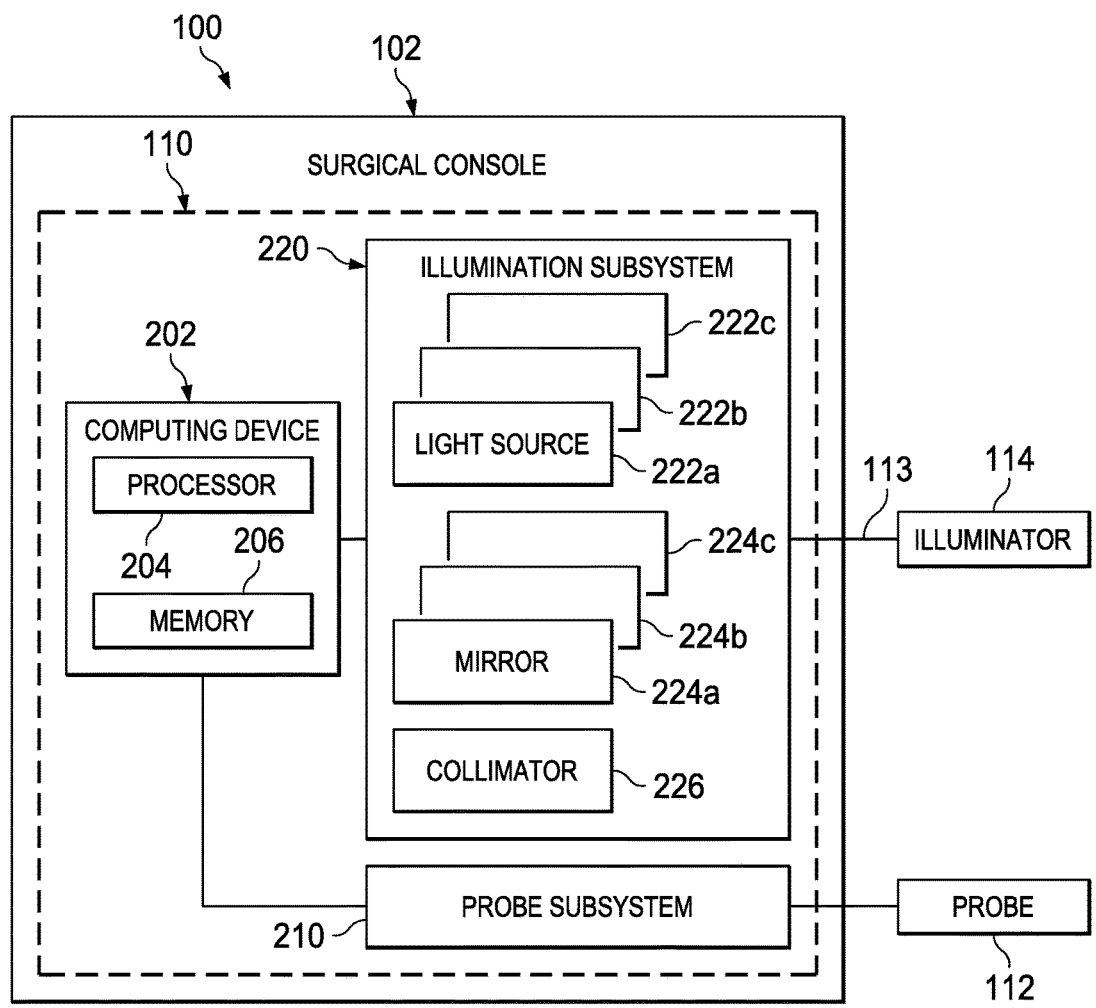
FIG. 2 is a block diagram of an example ophthalmic surgical system.

An exemplary implementation of the ophthalmic surgical system 100, including additional structure of the control system 110 is illustrated in the block diagram of FIG. 2. The illustrated implementation of the control system 110 includes a computing device 202, a probe subsystem 210, and an illumination subsystem 220. In some implementations, including the implementation shown, the computing device 202 is integrated into the surgical console 102, while in other implementations the computing device 202 may be distinct and separate from the console 102. The computing device 202 includes a processing circuit having one or more processors 204 and memory 206. The processor 204 may execute computer instructions, such as those stored on the memory 206, to control various subsystems and their associated surgical devices. The memory 206, which is typically a semiconductor memory such as RAM, FRAM, or flash memory, interfaces with the processor 204. As such, the processor(s) 204 may write to and read from the memory 206, and perform other common functions associated with managing semiconductor memory 206. Processing circuit(s) of the computing device 202 may be integrated circuits with power, input, and output pins capable of performing logic functions. In various implementations, the processor 204 is a targeted device controller, a microprocessor configured to control one or components of the surgical system 100 and/or a combination thereof. For example, the processor 204 may generate and transmit control signals to control activation and deactivation of the illumination subsystem 220 and/or the illuminator 114, as well as the intensity, wavelength, and/or other characteristics of light emitted by the illumination subsystem 220.

The probe subsystem 210 may include various components facilitating operation of the probe 112. In some implementations, the probe subsystem 210 may be in electrical communication with the computing device 202. In an implementation where the probe 112 is a pneumatically-actuated probe, when the probe 112 is pneumatically actuated, the probe subsystem 210 may include a pneumatic pressure source and/or a probe driver. In other implementations, the probe subsystem 210 may include various mechanical, electrical, piezoelectric, optical and/or other components for operation of the probe 112.

The illumination subsystem 220 includes a light source 222a, a mirror 224a, and a collimator 226. The light source 222a generates and/or otherwise provides light to the illuminator 114 via a conduit 113, such as an optical fiber. The conduit 113 may be operable to transmit light, optical signals, electrical signals, and/or data between the illumination subsystem 220 and the illuminator 114 in different implementations. The light source 222a may be in electrical communication with the computing device 202 and in electrical and/or optical communication with the illuminator 114. The light source 222a may be integrated in the surgical console 102, as shown in FIG. 2, or may be distinct and separate from the surgical console 102 in other implementations. In an exemplary implementation, the light source 222a is a supercontinuum laser source operable to provide bright, broadband, and/or white light to the illuminator 114 to illuminate the surgical field. Although light source 222a is primarily described as being a supercontinuum source, the present disclosure contemplates that light source 222a may include any suitable light source for producing a light beam that may be condensed into an optical fiber, as discussed below.

The mirror 224a may be configured to reflect light from the light source 222a towards the collimator 226. In some implementations, the mirror 224a is dichroic mirror that interacts with different light frequencies differently. For example, the mirror 224a may be a dichroic mirror that interacts with light in the visible spectrum differently than light in the infrared ("IR") spectrum. The mirror 224a may be a cold mirror that transmits all or a portion of the light in the IR spectrum and reflects all or a portion of the light in the visible spectrum. The mirror 224a may be a hot mirror that transmits all or a portion of the light in the visible spectrum and reflects all or a portion of the light in the IR spectrum. The mirror 224a may be a flat dichroic mirror, a hyperbolic dichroic mirror, an elliptical dichroic mirror, and/or otherwise suitably shaped dichroic mirror. As described in greater detail below, the mirror 224a may be spaced from the light source 222a or an optical fiber transmitting light from the light source 222a by a selected distance.

The collimator 226 may include a plurality of lenses configured to align the light emitted by the light source 222a. In some implementations, the collimator 226 is an achromatic collimator operable to collimate light beams having components of different wavelengths.

The light beam transmitted by the light source 222a may be characterized by a cone half angle or numerical aperture ("NA"). Formally, $NA_a=\sin(\frac{1}{2}\cdot\text{cone half angle}_a)$. Different light sources, such as light sources 222b and 222c may have different numerical apertures $NA_b$ and $NA_c$, respectively. In an exemplary implementation, a given surgical console, such as surgical console 102, includes one light source 222a and one mirror 224a. One or more components of the illumination subsystem 220, such as the collimator 226, may be selected, sized, shaped, positioned, and/or otherwise arranged for efficient operation with a light beam having a particular NA. As a result, using these components of the illumination subsystem 220, such as the collimator 226, with different light sources 222b, 222b is not desirable because of the adverse impact on coupling efficiency, undesired loss of transmittance within the fiber due to high angle rays being lost in the cladding, and/or an undesired angular profile of the output beam.

Generally, the light sources 222a, 222b, and 222c may have emitted beam NAs of $NA_a$, $NA_b$, and $NA_c$, respectively. The light beams reflected off of the mirror (e.g., mirror 224a, 224b, or 224c) may have beam NAs of $NA_a'$, $NA_b'$, $NA_c'$, respectively. In general, the primed NAs do not necessarily equal the unprimed NAs. However, for a given light source and a flat dichroic mirror, then NA'=NA. In some implementations, the collimator 226 may be configured to work efficiently with the $NA_a$ of light source 222a. In such implementations, the mirror 224a may be a flat dichroic mirror so that $NA_a'=NA_a$. In other implementations, even though the collimator 226 may be designed to be used with light with $NA_a$, the light sources 222b, 222c may be implemented in combination with mirrors 224b, 222c, respectively. The light sources 222b, 222c and/or mirrors 224b, 224c may be sized, shaped, positioned, arranged, and/or otherwise configured so that the reflected beam entering the collimator 226 has the same $NA_a$ that the collimator 226 is designed to work with. That is, when implemented with light sources 222b, 222c, the mirrors 224b, 224c may be configured to provide diffraction limited transformation of the wavefront of the reflected beam into the $NA_a$ associated with light source 222a. According to an aspect of the present disclosure, the mirrors 222b and 222c may be a hyperbolic or elliptical dichroic mirror to ensure that $NA_b'=NA_a$ and $NA_c'=NA_a$. Thus, regardless of the particular light source/mirror combination used, the reflected light entering the collimator 226 has the same NA.

The mirrors 224b, 224c may be a hyperbolic dichroic mirror, an elliptical dichroic mirror, a flat dichroic mirror, and/or otherwise suitably shaped dichroic mirror in various implementations. The size, parameters, and/or prescription defining the shape of the mirrors 224b, 224b may be different to account for the different $NA_b$, $NA_c$ of light sources 222b, 222c. The distance between the mirror 224b and the light source 222b, as well as the distance between the mirror 224c and the light source 222c, may be different than the distance between the mirror 224a and the light source 222a to account for the different $NA_b$, $NA_c$ of light sources 222b, 222c. Accordingly, different light sources 222b, 222c may be incorporated into the surgical console 102 without the need to change the collimator 226 or other optical components of the illumination subsystem 220.

Figure 3:
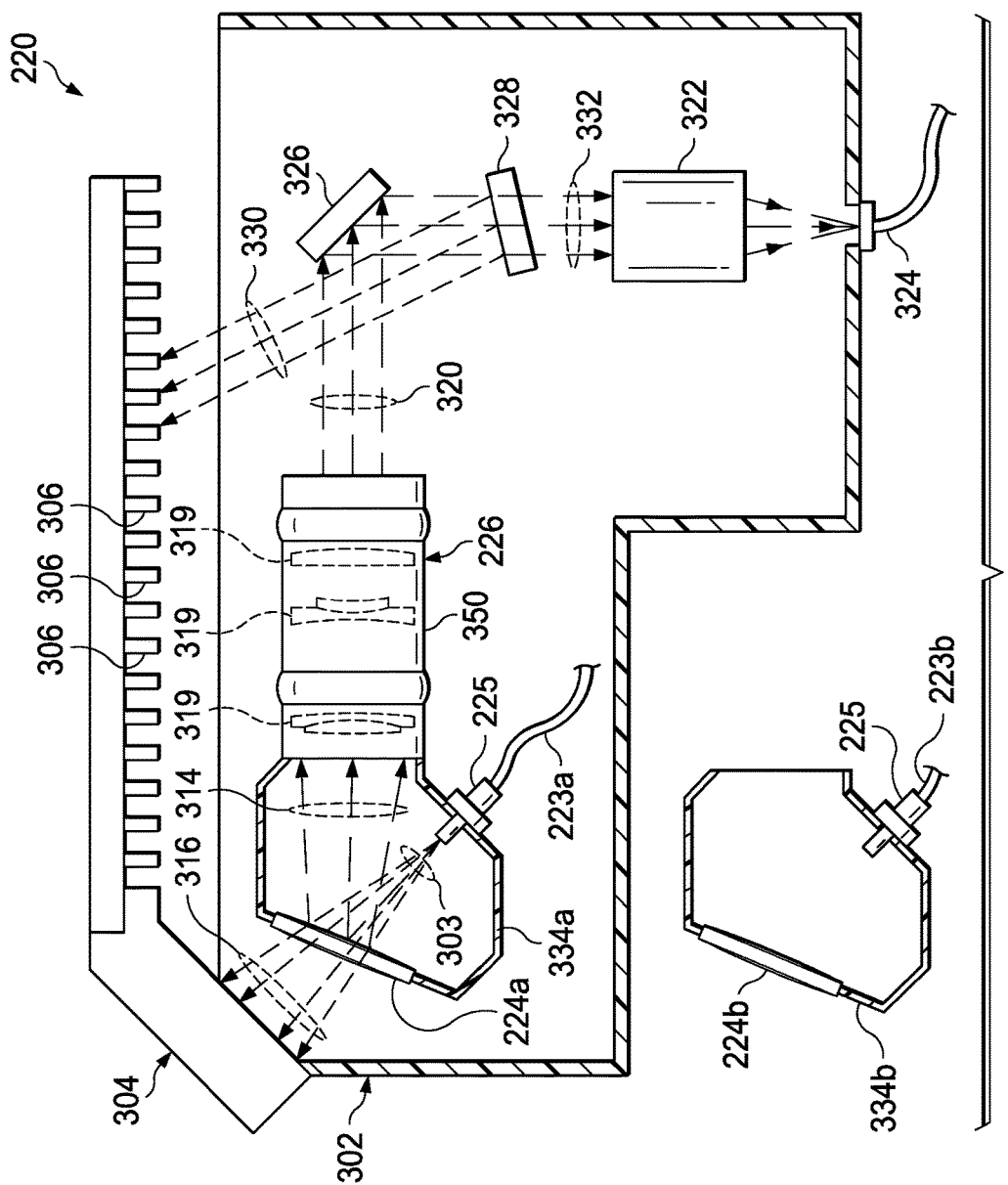
FIG. 3 is an illustration of an example illumination subsystem including a hyperbolic mirror.

FIG. 3 illustrates an example implementation of the illumination subsystem 220. One or more optical components may be mounted or otherwise fixed to a base plate 302. Light from the light source (e.g., the light source 222a in FIG. 2) may be transmitted via an optical fiber 223a that is coupled to a housing 334a at port 225. Light beam 303 emitted by the optical fiber 223a may be directed towards the mirror 224a, which is coupled to and/or supported by the housing 334a. The light beam 303 includes light in the visible and IR spectrums. In implementations in which the mirror 224a is a dichroic cold mirror, all or a portion of light in the visible spectrum (e.g., filtered beam 314) may be reflected. All or a portion of light in the IR spectrum (IR portion 316) passes through the mirror 224a. The mirror 224a may be oriented at an oblique angle relative to optical fiber 223a such that the reflected visible light (filtered beam 314) is directed towards subsequent optics in the illumination subsystem 220 (e.g., the collimator 226). The IR portion 316 passes through the mirror 224a and is incident upon all or a portion of beam dump/heat sink 304 having fins 306.

Figure 5:
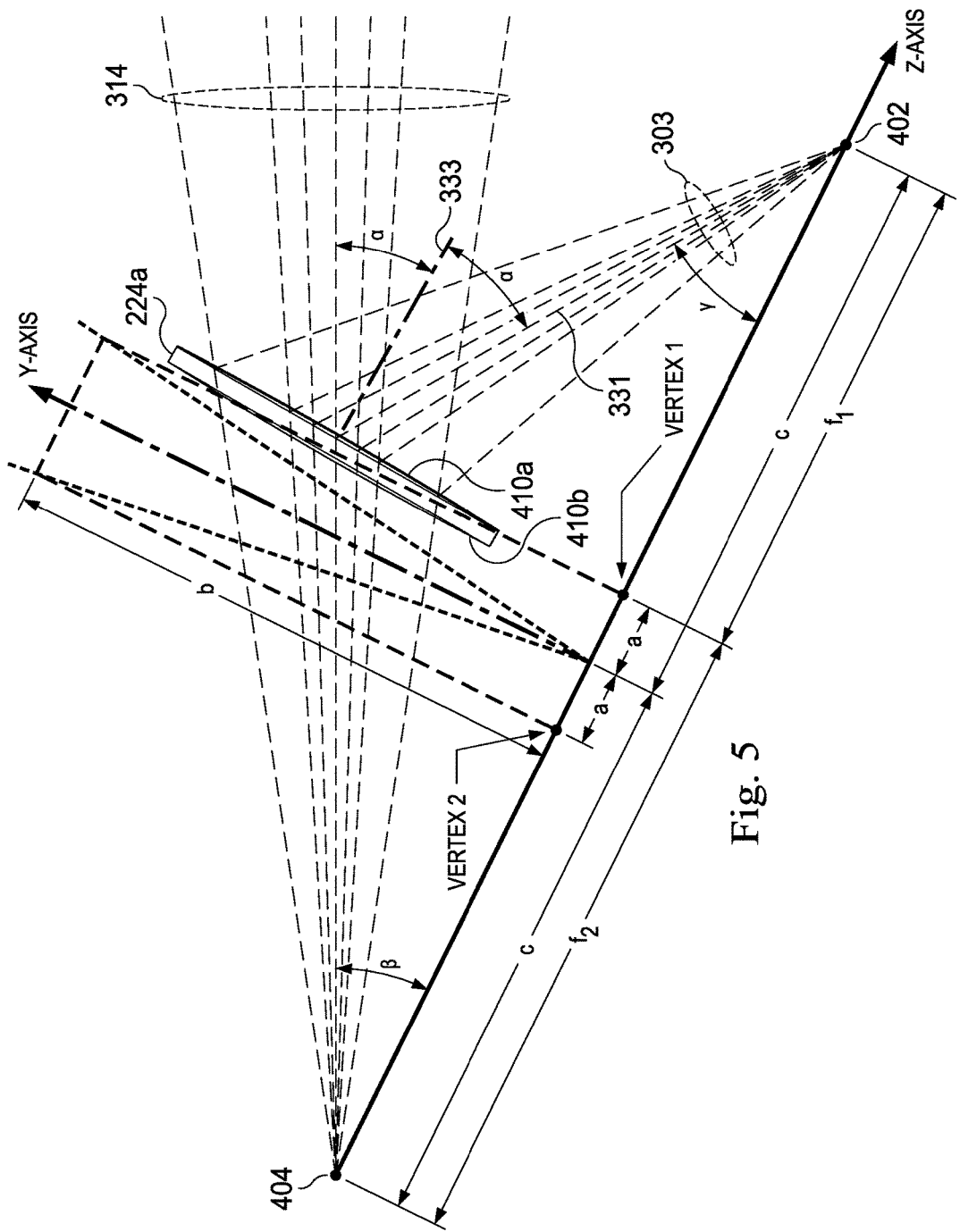
FIG. 5 is an illustration of an illumination subsystem similar to that of FIG. 4 but annotated to show characteristics of a hyperbolic mirror.

In some implementations, packaging constraints, such as the need to have fiber 223a in a different physical location than collimator 226, may necessitate the mirror 224a being tilted at an off-axis angle relative to the beam 303 emitted from the fiber 223a. As indicated in FIG. 5, the incident angle α measured between the normal of a central, axial ray 331 in the beam 303 and a line 333 normal to mirror 224a at a point where the central, axial ray 331 of the incident beam 330 intercepts the mirror 224a may be equal to the exit angle α relative to the normal of that same ray as it reflects off the dichroic mirror 224a. Referring again to FIG. 3, the mirror 224a may be variously positioned relative to the fiber 223a in different implementations such that the mirror 224a reflects light emitted by the fiber 223a towards the collimator 226.

The filtered beam 314, reflected by mirror 224a, may be directed towards and/or incident upon the collimator 226. The collimator 226 may include optics operable to generate a collimated light beam 320, including a plurality of lenses 319. The present disclosure contemplates that collimator 226 may comprise lenses, mirrors, gratings, filters, any suitable optics, or combination of optics operable to produce the collimated light beam 320. In some implementations, portions of the light beam reflected by the mirror 224a and collimated by the collimator 226 have the same collimated beam diameter regardless of the light source used and without variation based on wavelength.

The collimated light beam 320 generated by collimator 226 may be directed to a condenser 322 configured to focus or direct the collimated light beam 320 into an optical fiber 324. The optical fiber 324 may be a component of the illuminator 114 and/or in optical communication with the illuminator 114 such that the collimated light beam 320 is transmitted to the surgical field. The condenser 322 may include one or more optical lenses, mirrors, gratings, filters, other optical components, and/or combinations thereof configured to focus the collimated light beam 320 into the optical fiber 324.

In some implementations, the orientation of collimator 226 relative to condenser 322 may necessitate that collimated light beam 320 be redirected after exiting the collimator 226. For example, illumination subsystem 220 may include a fold mirror 326 configured to reflect collimated light beam 320 toward the condenser 322. In some implementations, a mirror 328 may be provided in the illumination subsystem 220 for additional IR filtering. The mirror 328 may be a hot mirror coated such that all or a portion of the remaining IR light of collimated light beam 320 (residual IR light 330) is reflected while the visible portion 332 of collimated light beam 320 passes through to the condenser 322. The mirror 328 may be oriented such that the reflected residual IR light 330 is directed towards beam dump/heat sink 304.

The collimator 226 includes a distal housing 350, a proximal housing 334a, the collimating lenses 319, and the mirror 224a. While the illustrated implementation shows a two-part housing, the collimator 226 may have a unitary, one-part housing or multi-part housing with more than two parts in different implementations. The distal housing 350 and the proximal housing 334a may be removably/interchangeably coupled to one another to assemble the collimator 226. For example, the distal housing 350 and the proximal housing 352a may each include corresponding threads to facilitate engagement. In other implementations, a bracket or other mechanical component may be used to removably/interchangeably couple the distal housing 350 and the proximal housing 334a.

The mirror 224a may be coupled to and/or supported by the proximal housing 334a. One or more lenses 319 may be disposed within, coupled to, and/or supported by one, the other, or both of the distal housing 350 and the proximal housing 334a. In some implementations, all of the collimator lenses are disposed within the distal housing 350, and the proximal housing 334a includes no lenses. The collimator 226 may also include the port 225 to which a distal portion of the light source fiber 223a is mechanically and/or optically coupled.

According to an aspect of the present disclosure, different light source(s) and different mirror(s) may be usable with the same collimator 226, while maintaining high coupling efficiency, avoiding undesired loss of transmittance within the fiber due to high angle rays being lost in the cladding, and/or achieving a desired angular profile of the output beam. For example, during assembly of the illumination subsystem 220, a manufacturer may choose from among multiple light source/mirror combinations for use with the collimator 226. For example, FIG. 3 illustrates an alternative proximal housing 334b that may replace the proximal housing 334a in the illumination subsystem 220. For example, the proximal housing 334b may be coupled to the distal housing 350 instead of the proximal housing 334a. An optical fiber 223b may transmit light from a light source (e.g., light source 222b in FIG. 2) that is different from the light source 222a associated with optical fiber 223a. The optical fiber 223b is coupled to the port 225 of the proximal housing 334b. Light emitted by the optical fiber 223b is directed towards the mirror 224b, which is coupled to and/or supported by the proximal housing 334b. The mirror 224b may be a hyperbolic, elliptical, flat, and/or otherwise suitably shaped dichroic mirror that transmits IR light and reflects visible light.

As similarly described with respect to the proximal housing 334a, the proximal housing 334b may be configured to be removably/interchangabely engaged with the distal housing 350. While some components of the illumination subsystem 220 are described as being removably/interchangeably engaged, it is understood that in some implementations, the components are not intended to be separated after the illumination subsystem 220 has been manufactured. In that regard, the removable or interchangeable nature of components may refer to the ability of a manufacturer to select from among multiple components to assemble the illumination subsystem 220. That is, a manufacturer may choose to couple the distal housing 350 to any of multiple different components, such as the proximal housings 334a, 334b.

While the light beams from light sources 222a, 222b have different NAs, the mirror 224b may be positioned, sized, shaped, arranged, and/or otherwise configured such that light reflected from mirror 224b has the same or substantially the same NA with which the collimator 226 is configured to work. For example, the specific parameters or prescription defining hyperbolic or elliptical features of the mirror 224b may account for the different NAs of the light sources 222a, 222b. Also, the optical fiber 223a and the mirror 224a may be separated by a first distance while the optical fiber 223b and the mirror 224b may be separated by a second distance, which may be different from the first distance, to account for the different NAs associated with light sources 222a, 222b. The light sources 222a, 222b, the optical fibers 223a, 223b, and/or the mirrors 224a, 224b may be coupled to and/or otherwise supported by proximal housings 334a, 334b, respectively, to facilitate the appropriate spacing between components.

Figure 4:
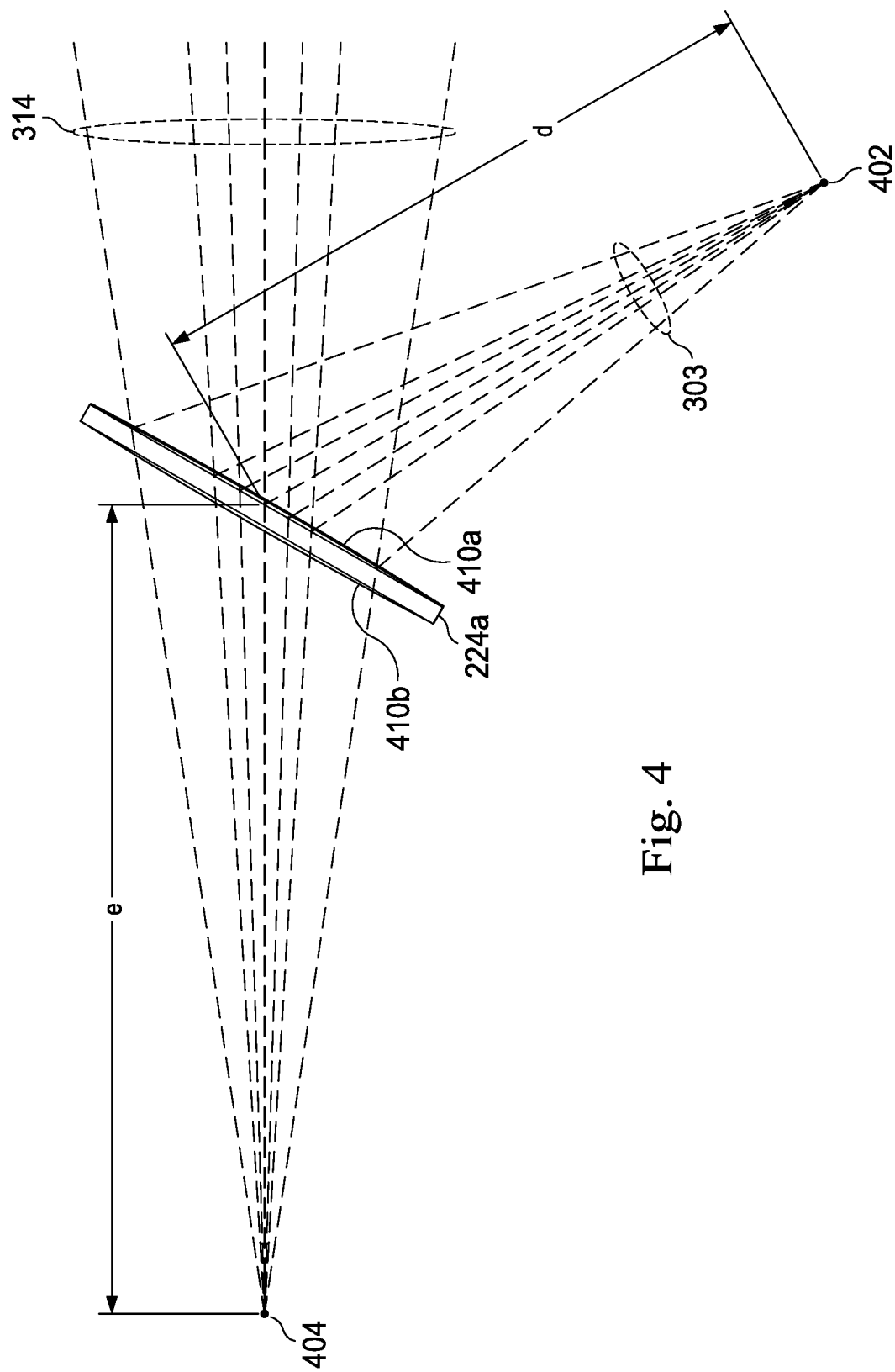
FIG. 4 is an illustration of a portion of an example illumination subsystem.

FIG. 4 illustrates a portion of the illumination subsystem 220 including the mirror 224a. The mirror 224a includes two faces 410a, 410b. In various implementations, one, the other, or both faces 410a, 410b may be flat, hyperbolic, elliptical, and/or otherwise suitably shaped. In the illustrated implementation, the hyperbolic faces 410a, 410b may have a surface sag relative to a flat surface between approximately 1 μm and approximately 20 μm, approximately 5 μm and approximately 15 μm, and approximately 10 μm and approximately 15 μm, including values such as 12 μm, 13 μm, 13.5 μm, 13.7 μm, 13.9 μm, 14 μm, and/or other suitable values both larger and smaller.

The source location 402 may identify the actual or effective location from which light 303 from the light source 222a is transmitted towards the mirror 224a. For example, the source location 402 may correspond to the distal end of the optical fiber 223a, the port 225, or the location of the light source 222a itself. The mirror 224a may be spaced from the source location 402 by a distance d. The distance d may vary for mirrors 224a, 224b, and 224c. For example, the distance d may be between approximately 1 mm and approximately 10 mm, approximately 1 mm and approximately 7 mm, and approximately 1 mm and approximately 5 mm, including values such as 3 mm, 3.2 mm, 3.5 mm, 3.8 mm, 4 mm, and/or other suitable values both larger and smaller. In some implementations, the distance d and the NA of the light source may be inversely related. Thus, the mirror 224a and the source location 402 may be separated by a relatively smaller distance d when a light source having a relatively larger NA is used (and vice versa). As described below, in implementations in which the distance d varies, the distance e may remain the same.

The virtual source 404 may indicate the location from which the filtered beam 314 appears to diverge. In that regard, although the filtered beam 314 is in reality reflected off of the mirror 224a, the beam 314 appears to diverge from behind the mirror 224a at the virtual source 404. The virtual source 404 is spaced from the mirror 224a by the distance e. The location and position of the virtual source 404 may be optimized to facilitate efficient coupling of the light beam. In some implementations, the distance e may be the same for mirrors 224a, 224b, and 224c. For example, the distance e may be between approximately 1 mm and approximately 10 mm, approximately 1 mm and approximately 7 mm, and approximately 1 mm and approximately 5 mm, including values such as 3 mm, 3.5 mm, 4 mm, 4.5 mm, 5 mm, and/or other suitable values both larger and smaller. For example, the mirror (e.g., mirrors 224a, 224b, 224c) in different implementations may be placed at the same location relative to the collimator 226 (e.g., as measured by the distance of the central axial ray from the reflective surface of the mirror to the first collimator lens 319). In such circumstances, in order for the reflected beam NAs from different light sources (e.g., the light sources 222b, 222c) to be the same or substantially similar to the beam NA with which the collimator 226 is designed to work (e.g., $NA_b'=NA_a$ and $NA_c'=NA_a$), then the distance e may be the same for all mirrors 224a, 224b, and 224c. For implementations in which the emitted beam NAs of different light sources are different, then each distance d between the mirror and the light source may be different, as described above.

FIG. 5 illustrates a portion of the illumination subsystem 220 as in FIG. 4. FIG. 5 additionally includes various annotations indicating values used to calculate the specific parameters of the hyperbolic surfaces 410a, 410b of the mirror 224a. The parameters of the mirror 224a may be selected to facilitate transformation of the reflected beam into a common NA for multiple supercontinuum sources. Formally, the shape of one or both faces 410a, 410b may be defined by $$\frac{x^2}{a^2} - \frac{y^2}{b^2} = 1.$$

The parameter a may be defined by $$\frac{f_2 - f_1}{2},$$

where $f_1$ is the distance between the source location 402 and the mirror 224a along the z-axis and $f_2$ is the distance between the mirror 224a and the virtual source 404 along the z-axis. In some implementations, the parameter a may be between approximately 0.1 mm and approximately 1 mm, or between approximately 0.1 mm and approximately 0.5 mm, including values such as 0.200 mm, 0.300 mm, 0.400 mm, and/or other suitable values both larger and smaller. In some implementations, the parameter $f_1$ may be between approximately 1 mm and approximately 5 mm, or between approximately 2 mm and approximately 3 mm, including values such as 2.500 mm, 2.700 mm, 2.710 mm, 2.720 mm, 2.722 mm, 2.724 mm, 2.726 mm, 2.730 mm, and/or other suitable values both larger and smaller. In some implementations, the parameter $f_2$ may be between approximately 1 mm and approximately 5 mm, or between approximately 3 mm and approximately 5 mm, including values such as 3.500 mm, 3.510 mm, 3.520 mm, 3.522 mm, 3.524 mm, 3.526 mm, 3.530 mm, and/or other suitable values both larger and smaller.

The parameter b may be defined by $\sqrt{c^2-a^2}$, where $$c = \frac{f_1 + f_2}{2},$$

which is half the distance between the source point 402 and the virtual source point 404. In some implementations, the parameter b may be between approximately 1 mm and approximately 5 mm, or between approximately 2.5 mm and approximately 3.5 mm, including values such as 2.900 mm, 3.000 mm, 3.095 mm, 3.098 mm, and/or other suitable values both larger and smaller. In some implementations, the parameter c may be between approximately 1 mm and approximately 5 mm, or between approximately 2.5 mm and approximately 3.5 mm, including values such as 3.000 mm, 3.100 mm, 3.120 mm, 3.122 mm, 3.124 mm, 3.126 mm, 3.130 mm, and/or other suitable values both larger and smaller.

A parameter R may be defined by $$-\frac{b^2}{a},$$

which represents the base radius of curvature associated with the hyperbolic surfaces 410a, 410b. In some implementations, the parameter R may be between approximately −10 mm and approximately −30 mm, or between approximately −20 mm and approximately −25 mm, including values such as −23.00 mm, −24.00 mm, −25.00 mm, and/or other suitable values both larger and smaller.

A parameter k may be defined by $$-1-\frac{b^2}{a^2},$$

which represents the conic constant associated with the hyperbolic surfaces 410a, 410b. The parameter k may be referenced as the degree of deviation from a purely spherical surface. In some implementations, the parameter k may be between approximately −40 and approximately −70, or between approximately −55 and approximately −65, including values such as −60.00, −61.00, −62.00, and/or other suitable values both larger and smaller.

The angle α may describe the incident angle of light upon the mirror 224a measured between the central, axial ray 331 in the beam 303 from the light source and/or associated optical fiber and a line 33 normal to mirror 224 at a point where the central, axial ray 331 of the incident beam 330 intercepts the mirror 224a. The incident angle α may be equal to the exit angle α relative to normal of that same ray as it reflects off the mirror 224a. In some implementations, the angle α may be between approximately 10° and approximately 40°, or between approximately 25° and approximately 35°, including values such as 29°, 30°, 31°, and/or other suitable values both larger and smaller. The angle β may describe the angle between the virtual portion of the filtered beam 314 and the z-axis. In some implementations, the angle β may be between approximately 10° and approximately 40°, or between approximately 20° and approximately 30°, including values such as 26.20°, 26.30°, 26.33°, 26.35°, and/or other suitable values both larger and smaller. The angle γ may describe the angle between the light emitted from the source location 402 and the z-axis. In some implementations, the angle γ may be between approximately 20° and approximately 50°, or between approximately 30° and approximately 40°, including values such as 33.50°, 33.65°, 33.67°, 33.69°, and/or other suitable values both larger and smaller.

Figure 6:
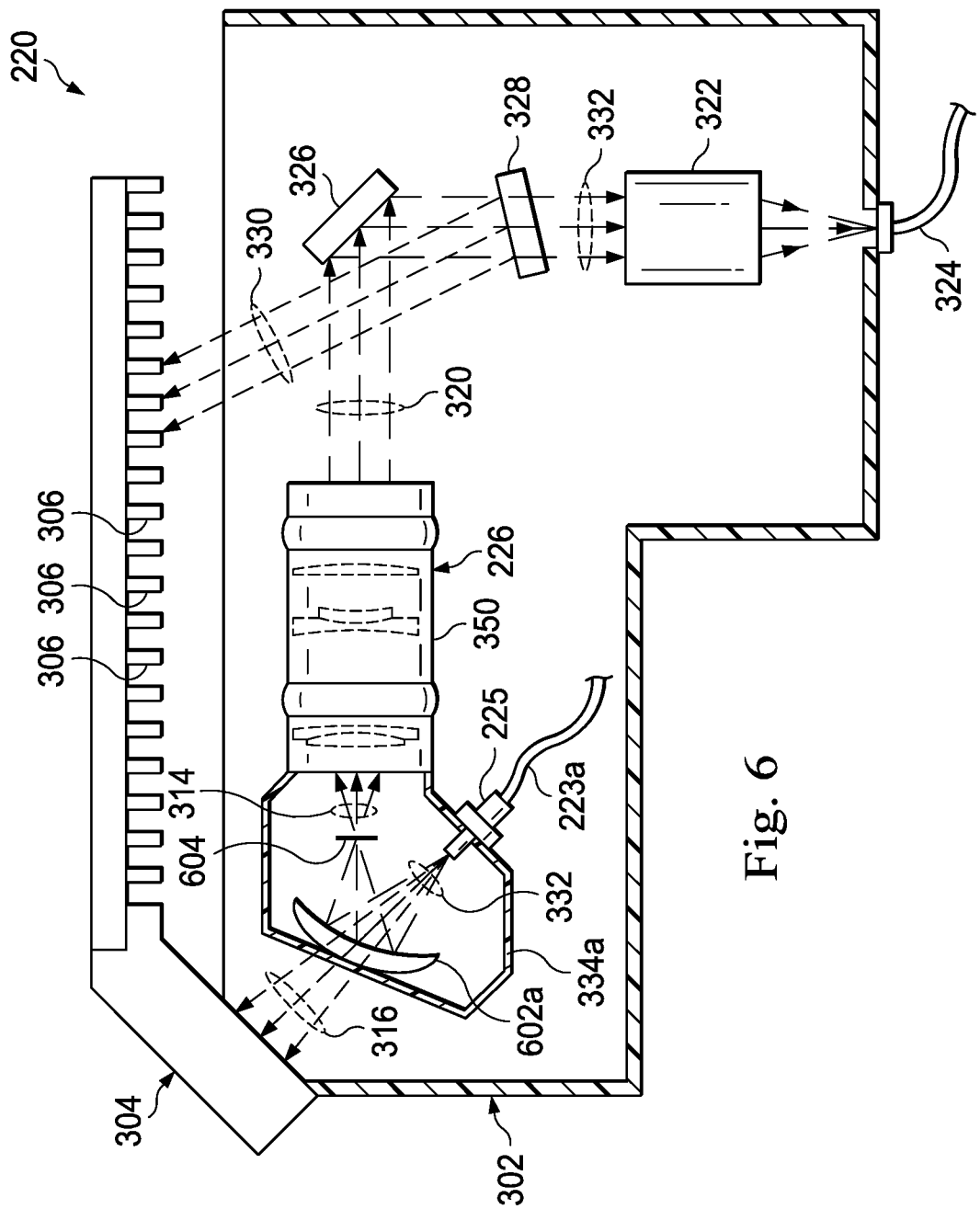
FIG. 6 is an illustration of an illumination subsystem similar that of FIG. 3 but including an elliptical mirror.

FIG. 6 illustrates the illumination subsystem 220 similar to that FIG. 3. In that regard, FIG. 6 includes many similar components as FIG. 3, the descriptions of which are omitted. The illumination subsystem of FIG. 3 includes an elliptical dichroic mirror 602a. The elliptical dichroic mirror 602a is configured to transmit IR light and reflect visible light in the beam 332. The elliptical dichroic mirror 602a is also configured to provide diffraction limited transformation of the wavefront of the reflected beam 314 into the same $NA_a$ for multiple light sources 222a, 222b, and 222c. One or more faces of the elliptical dichroic mirror 602a may be defined by $$\left(\frac{x}{a}\right)^2 + \left(\frac{y}{b}\right)^2 = 1.$$

Similar to the hyperbolic dichroic mirrors described herein, other elliptical mirrors, such as, for example, elliptical dichroic mirrors, may be separately used with the collimator and different light sources 222b, 222c. The distance between the light sources 222a, 222b, 222c (or the optical fibers 223a, 223b, etc.) and various elliptical dichroic mirrors may vary for each combination to allow the reflected beam to have the same $NA_a$. The specific parameters (e.g., the parameter a, the parameter b, etc.) of the various elliptical dichroic mirrors may also be selected for different light sources 222a, 222b, and 222c. With an elliptical dichroic mirror 602a, the filtered beam 314 has a convergence point 604 between the mirror 602a and the collimator 226.

Figure 7:
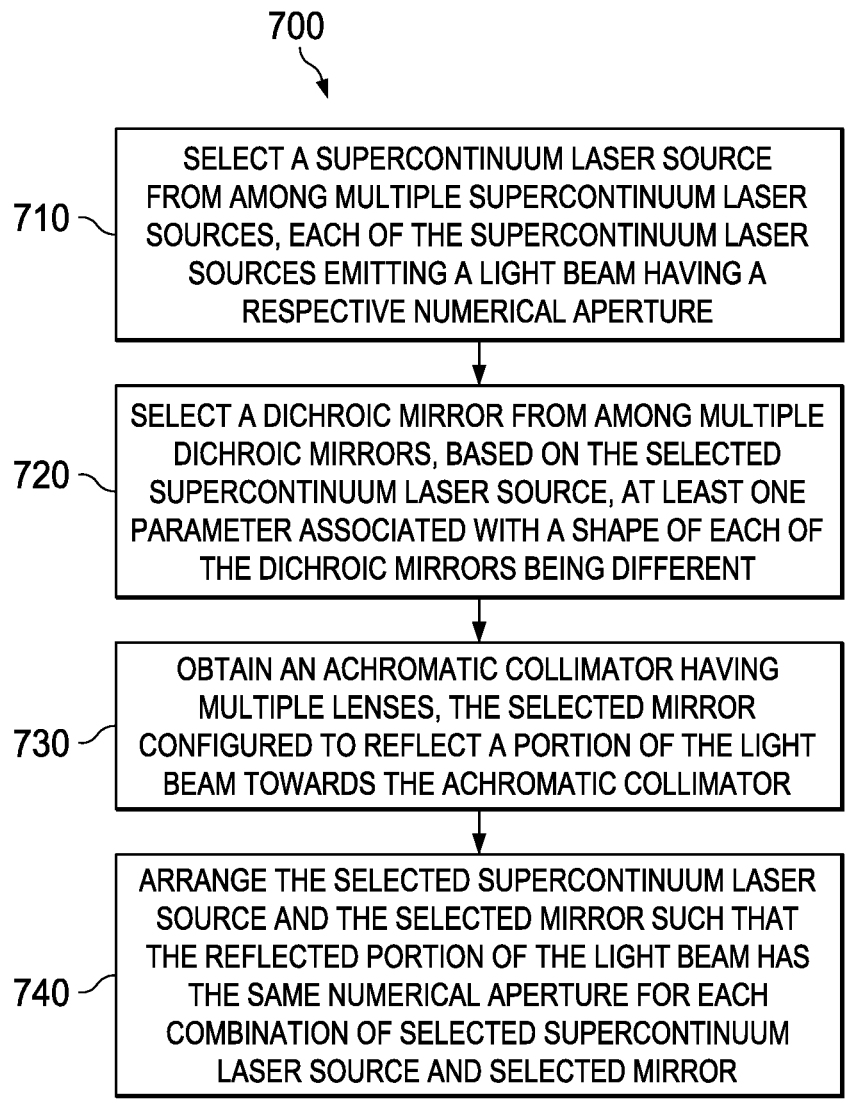
FIG. 7 is a flow diagram of an example method of manufacturing an ophthalmic illumination system.

FIG. 7 illustrates a flowchart of an example method 700 of manufacturing an ophthalmic illumination system. As illustrated, the method 700 includes a number of enumerated steps, but implementations of the method 700 may include additional steps before, after, and in between the enumerated steps. In some implementations, one or more of the enumerated steps may be omitted or performed in a different order.

At step 710, the method 700 includes selecting a supercontinuum laser source from among multiple supercontinuum laser sources. Each of the supercontinuum laser sources emits a light beam having a respective numerical aperture. In that regard, the numerical apertures may be larger or smaller than one another. For example, a first laser source may have an NA at 650 nm at the $1.3 \times 1/e^2$ points that is approximately 0.1503. A second laser source may have an NA that is approximately 25% larger than the first laser source. While particular NA values are listed as examples, it is understood the present disclosure contemplates any suitable NA values.

At step 720, the method 700 includes selecting a dichroic mirror from among multiple dichroic mirrors. In some implementations, the dichroic mirrors are hyperbolically, elliptically, and/or otherwise suitably shaped. At least one parameter defining the shape may be different between the multiple dichroic mirrors. The dichroic mirror may be selected based on the selected supercontinuum laser source (step 710).

At step 730, the method 700 includes obtaining an achromatic collimator having multiple lenses. The selected mirror (step 720) may be configured to reflect a portion of the light beam from the selected supercontinuum laser source (step 710) towards the achromatic collimator.

At step 740, the method 700 includes arranging the selected supercontinuum laser source (step 710) and the selected mirror (step 720) such that the reflected portion of the light beam has the same numerical aperture for each combination of selected supercontinuum laser source and selected mirror. With reference to the example light sources described above, the supercontinuum laser source and the dichroic mirror may be arranged so that reflected portion of the light beam from the second laser source has the same NA as the first laser source. This is true even though the beam emitted by the second laser source has a 25% larger NA than the first laser source. In order to transform the reflected beam into a common NA, step 740 may include spacing the selected supercontinuum laser source and the selected mirror a first distance. Another of the multiple supercontinuum laser sources and another of the multiple mirrors may be spaced a second distance for the reflected portion of the light beam to have the same NA. Step 740 may include coupling the achromatic collimator and a housing comprising the selected supercontinuum laser source and the selected mirror. The housing may include or be coupled to at least a portion of an associated optical fiber. In some implementations, the selected mirror may be disposed within a first housing and the multiple lenses of the achromatic collimator are disposed within a third housing. Another of the multiple mirrors may be disposed within a second housing. The third housing with the collimator may be separately coupled to the first and second housings, based on the selected mirror.

The method 700 can include additional steps in other implementations, such as obtaining a condenser. Collimated light may be directed to the condenser and into an optical fiber associated with a hand-held illuminator. In some implementations, the method 700 includes obtaining an IR filtering mirror and positioning the mirror within the illumination subsystem to remove IR light while allowing visible light to pass through. The method 700 can also include installing the illumination subsystem within a surgical console and performing a surgical procedure using the surgical console.

Persons of ordinary skill in the art will appreciate that the implementations encompassed by the present disclosure are not limited to the particular exemplary implementations described above. In that regard, although illustrative implementations have been shown and described, a wide range of modification, change, combination, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ophthalmic illumination system, comprising:
   a collimator comprising a lens;
   a first mirror arranged to reflect light towards the collimator, wherein the first mirror is configured for use with a first light source, the first light source emitting a first light beam having a first parameter; and
   a second mirror arranged to reflect light towards the collimator, wherein the second mirror is configured for use with a second light source, the second light source emitting a second light beam having a second parameter that is different than the first parameter, wherein the second mirror is shaped and arranged to cause a reflected portion of the second light beam to have the first parameter;
   wherein the first mirror and the first light source, and the second mirror and the second light source, are separately usable with the collimator,
   wherein the first and second parameters are first and second numerical apertures, respectively.

2. The system of claim 1, wherein the collimator comprises an achromatic collimator.

3. The system of claim 1, wherein at least one of the first mirror and the second mirror comprises a hyperbolic dichroic mirror.

4. The system of claim 1, wherein the collimator and at least one of the first mirror and second mirror are disposed within a surgical console.

5. The system of claim 1, wherein the collimator comprises a plurality of lenses, wherein the first mirror is disposed within a first housing, the second mirror is disposed within a second housing, and at least one of the plurality of lenses of the collimator is disposed within a third housing.

6. The system of claim 5, wherein the first housing and second housing are sized and shaped to be interchangeably coupled to the third housing.

7. The system of claim 1, wherein the first mirror is spaced from the first light source by a first distance, and wherein the second mirror is spaced from the second light source by a second distance different from the first distance.

8. The system of claim 1, further comprising the first and second light sources, wherein the first and second light sources are separately usable with the collimator.

9. The system of claim 8, wherein at least one of the first and second light sources is a supercontinuum laser source.

10. The system of claim 1, wherein at least one of the first mirror and the second mirror comprises an elliptical dichroic mirror.

11. An ophthalmic illumination system, comprising:
a collimator comprising a lens;
a first mirror arranged to reflect light towards the collimator, wherein the first mirror is configured for use with a first light source, the first light source emitting a first light beam having a first parameter; and
a second mirror arranged to reflect light towards the collimator, wherein the second mirror is configured for use with a second light source, the second light source emitting a second light beam having a second parameter that is different than the first parameter, wherein the second mirror is shaped and arranged to cause a reflected portion of the second light beam to have the first parameter;
wherein the first mirror and the first light source, and the second mirror and the second light source, are separately usable with the collimator,
wherein at least one of the first mirror and the second mirror comprises a hyperbolic dichroic mirror.

12. The system of claim 11, wherein the collimator comprises an achromatic collimator.

13. The system of claim 12, wherein the collimator comprises a plurality of lenses, wherein the first mirror is disposed within a first housing, the second mirror is disposed within a second housing, and at least one of the plurality of lenses of the collimator is disposed within a third housing.

14. The system of claim 13, wherein the first housing and second housing are sized and shaped to be interchangeably coupled to the third housing.

15. The system of claim 13, further comprising the first and second light sources, wherein the first and second light sources are separately usable with the collimator.

16. The system of claim 15, wherein at least one of the first and second light sources is a supercontinuum laser source.

17. An ophthalmic illumination system, comprising:
a collimator comprising a lens;
a first mirror arranged to reflect light towards the collimator, wherein the first mirror is configured for use with a first light source, the first light source emitting a first light beam having a first parameter; and
a second mirror arranged to reflect light towards the collimator, wherein the second mirror is configured for use with a second light source, the second light source emitting a second light beam having a second parameter that is different than the first parameter, wherein the second mirror is shaped and arranged to cause a reflected portion of the second light beam to have the first parameter;
wherein the first mirror and the first light source, and the second mirror and the second light source, are separately usable with the collimator,
wherein the collimator comprises a plurality of lenses, wherein the first mirror is disposed within a first housing, the second mirror is disposed within a second housing, and at least one of the plurality of lenses of the collimator is disposed within a third housing,
wherein the first housing and second housing are sized and shaped to be interchangeably coupled to the third housing.

18. The system of claim 17, wherein the collimator comprises an achromatic collimator.

19. The system of claim 18, wherein at least one of the first mirror and the second mirror comprises a hyperbolic dichroic mirror.

20. An ophthalmic illumination system, comprising:
a collimator comprising a lens;
a first mirror arranged to reflect light towards the collimator, wherein the first mirror is configured for use with a first light source, the first light source emitting a first light beam having a first parameter; and
a second mirror arranged to reflect light towards the collimator, wherein the second mirror is configured for use with a second light source, the second light source emitting a second light beam having a second parameter that is different than the first parameter, wherein the second mirror is shaped and arranged to cause a reflected portion of the second light beam to have the first parameter;
wherein the first mirror and the first light source, and the second mirror and the second light source, are separately usable with the collimator,
wherein at least one of the first mirror and the second mirror comprises an elliptical dichroic mirror.

* * * * *